(12) United States Patent
Wang et al.

(10) Patent No.: US 9,664,500 B2
(45) Date of Patent: May 30, 2017

(54) TUNABLE OPTOFLUIDIC APPARATUS, METHOD, AND APPLICATIONS

(71) Applicant: CORNELL UNIVERSITY, Ithaca, NY (US)

(72) Inventors: Michelle D. Wang, Ithaca, NY (US); Michal Lipson, Ithaca, NY (US); Mohammad Soltani, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 23 days.

(21) Appl. No.: 14/383,544

(22) PCT Filed: Mar. 7, 2013

(86) PCT No.: PCT/US2013/029515
§ 371 (c)(1),
(2) Date: Sep. 6, 2014

(87) PCT Pub. No.: WO2013/134463
PCT Pub. Date: Sep. 12, 2013

(65) Prior Publication Data
US 2015/0049338 A1 Feb. 19, 2015

Related U.S. Application Data

(60) Provisional application No. 61/608,223, filed on Mar. 8, 2012, provisional application No. 61/662,962, filed on Jun. 22, 2012.

(51) Int. Cl.
G01N 21/77 (2006.01)
G01B 9/02 (2006.01)
(Continued)

(52) U.S. Cl.
CPC ..... *G01B 9/02049* (2013.01); *G01B 9/02001* (2013.01); *G01N 21/7703* (2013.01);
(Continued)

(58) Field of Classification Search
CPC ............... G01N 15/02; G01N 21/7703; G01N 21/7746; G01N 2021/7779; G01N 2021/7789
(Continued)

(56) References Cited

U.S. PATENT DOCUMENTS 5,886,249 A 3/1999 Bonne et al.
6,721,053 B1 * 4/2004 Maseeh ............ G01N 21/7746
356/436
(Continued)

FOREIGN PATENT DOCUMENTS

WO 2008151611 A1 12/2008
WO 2011106057 A9 9/2011
(Continued)

OTHER PUBLICATIONS

Fan, et al., Overview of Novel Integrated Optical Ring Resonator Bio/Chemical Sensors, Biological Engineering Department, University of Missouri, 1201 E. Rollins Street, 240D Life Sciences Center, Columbia, MO 65211, pp. 1-20.
(Continued)

*Primary Examiner* — Jonathan Hansen
(74) *Attorney, Agent, or Firm* — Bond, Schoeneck & King, PLLC; William Greener; Alek Szecsy

(57) ABSTRACT

Embodiments include optofluidic apparatus that may be used to detect and manipulate nanoparticles or biomolecules within a fluid. To achieve that result, the embodiments use a fluidic channel located over a substrate. Particular embodiments also use: (1) an optical waveguide located over the substrate and particularly within the fluidic channel along with an optical resonator that may or may not be located within fluidic channel; and also (2) a phase shifter component coupled to either the waveguide or the optical resonator. Additional embodiments use an MZI or an MZI with an
(Continued)

optical resonator to further provide the phase shifter component coupled to one arm of the MZI or the optical resonator.

9 Claims, 7 Drawing Sheets

(51) Int. Cl.
*G01N 27/447* (2006.01)
*G02B 6/10* (2006.01)

(52) U.S. Cl.
CPC ... *G01N 21/7746* (2013.01); *G01N 27/44721* (2013.01); *G02B 6/10* (2013.01); *G01N 2021/7779* (2013.01)

(58) Field of Classification Search
USPC .................................................. 356/477, 480
See application file for complete search history.

(56) References Cited

U.S. PATENT DOCUMENTS

| | | | |
|---|---|---|---|
| 7,212,701 B2 | 5/2007 | Strecker | |
| 7,574,089 B1 | 8/2009 | Zribi et al. | |
| 7,693,369 B2 | 4/2010 | Fan et al. | |
| 7,751,654 B2* | 7/2010 | Lipson | G02F 1/025 385/1 |
| 7,798,164 B2 | 9/2010 | Adleman et al. | |
| 7,817,698 B2 | 10/2010 | Li et al. | |
| 7,885,490 B2* | 2/2011 | Heideman | B01L 3/5027 385/12 |
| 8,174,698 B2 | 5/2012 | Peter et al. | |
| 8,254,733 B2 | 8/2012 | Heideman et al. | |
| 8,293,177 B2 | 10/2012 | Chakravarty et al. | |
| 2004/0091392 A1 | 5/2004 | McBride et al. | |
| 2006/0216200 A1* | 9/2006 | Nagatomo | G01N 21/774 422/68.1 |
| 2010/0067847 A1 | 3/2010 | Levy et al. | |
| 2010/0124787 A1* | 5/2010 | Nitkowski | G01N 21/7746 436/164 |
| 2011/0039730 A1 | 2/2011 | Erickson et al. | |
| 2011/0294691 A1 | 12/2011 | Erickson et al. | |
| 2011/0306854 A1 | 12/2011 | Arnold et al. | |
| 2012/0194804 A1 | 8/2012 | He et al. | |
| 2012/0196383 A1 | 8/2012 | Nitkowski et al. | |
| 2012/0269481 A1 | 10/2012 | Erickson et al. | |
| 2012/0308181 A1 | 12/2012 | Hafezi et al. | |

FOREIGN PATENT DOCUMENTS

| | | |
|---|---|---|
| WO | 2011133670 A2 | 10/2011 |
| WO | 2012048220 A2 | 4/2012 |
| WO | 2012059828 A2 | 5/2012 |
| WO | 2012099848 A1 | 7/2012 |

OTHER PUBLICATIONS

Levy, et al., On-Chip Microfluidic Tuning of an Optical Microring Resonator, Applied Physics Letters 88, American Institute of Physics, Dated 2006, pp. 111107-01-111107-03.

Dong, et al., Low Power and Compact Reconfigurable Multiplexing Devices Based on Silicon Microring Resonators, Optical Society of America, Optics Express, Dated May 10, 2010, vol. 18, No. 10, pp. 9852-9858.

* cited by examiner

TUNABLE OPTOFLUIDIC APPARATUS, METHOD, AND APPLICATIONS

CROSS-REFERENCE TO RELATED APPLICATION

This application is related to, and derives priority from: (1) U.S. Provisional Patent Application Ser. No. 61/608,223, filed 8 Mar. 2012 and titled Tunable Optofluidic Apparatus, Method and Applications; and (2) U.S. Provisional Patent Application Ser. No. 61/662,962, filed 22 Jun. 2012 and titled Tunable Optofluidic Apparatus, Method and Applications, the contents of which are incorporated herein fully by reference.

BACKGROUND

Field of the Invention

Embodiments relate generally to optofluidic apparatus and devices. More particularly, embodiments relate to tunable optofluidic apparatus and devices.

Description of the Related Art

Integrated optofluidic apparatus and devices, and related methods that use the integrated optofluidic apparatus and devices, have evolved to facilitate the potential of chip-scale applications related to the detection and the manipulation of nanoparticles and biomolecules. As is well understood, optical waveguides and optical resonators are generally the fundamental building blocks that comprise integrated optofluidic apparatus and devices. Since an ability to detect and to manipulate a nanoparticle and a biomolecule is a desirable characteristic for many advanced applications in the nanoscience related fields and the healthcare related fields, desirable are integrated optofluidic apparatus and devices, and related methods that more efficiently or more comprehensively provide for the detection and the manipulation of nanoparticles and biomolecules while using the integrated optofluidic apparatus and devices.

SUMMARY

Embodiments provide a tunable integrated optofluidic apparatus and a method for detecting or manipulating a nanoparticle or a biomolecule while using the tunable integrated optofluidic apparatus. Particular embodiments use within the context of a substrate including a fluidic channel: (1) an optical resonator and at least one waveguide, where the at least one waveguide is located at least in-part within the fluidic channel within the substrate; or (2) a waveguide based Mach-Zender interferometer (MZI) with an optional optical resonator, where at least one output waveguide of the MZI is located at least in-part within the fluidic channel within the substrate. All embodiments also include a phase shifter (i.e., a refractive index tuning component) that tunes an index of refraction of a portion of the waveguide, the resonator or the waveguide based MZI, and thus provides for detection or manipulation of a nanoparticle or a biomolecule within a fluid within the fluidic channel. This result may be particularly significant as the temperature change is absent within the fluidic channel which carries the nanoparticle or the biomolecule, and while using a single input wavelength into the tunable integrated optofluidic apparatus. Within the embodiments, the phase shifter is not located within the fluidic channel within the substrate.

Thus, a particular exemplary embodiment provides a tunable optofluidic apparatus architecture and fabrication methodology to integrate a microheater as a phase shifter for waveguide index of refraction tuning within an optofluidic device located and formed within an integrated optofluidic chip. While a method in accordance with the embodiments may utilize an apparatus in accordance with the embodiments that comprises a variety of optical materials that have a thermo-optic effect, the embodiments focus on optical materials which are compatible with mass manufacturing nano- and micro-fabrication technologies, such as but not limited to complementary-metal-oxide-semiconductor (CMOS) technology, to reduce the apparatus fabrication cost. For this purpose, silicon (Si) and silicon nitride ($Si_3N_4$) are considered as promising optical material candidates that are widely used in CMOS technology applications.

Within the context of the embodiments, an "apparatus" is intended as a structural component fabricated with respect to a substrate and absent optical activation or phase shift actuation. A "device" is intended as the "apparatus" in accordance with the embodiments when the "apparatus" in accordance with the embodiments has been: (1) rendered operative upon activation with light in an operative waveguide; and (2) actuated with electricity or some alternative stimulus as a phase shifter.

The unique specifications and novel aspects of the optofluidic apparatus and related device presented in accordance with the embodiments may be summarized as follows: (1) the embodied apparatus provides an early demonstration of a tunable electro-optofluidic apparatus and device; (2) the apparatus is very compact; (3) the apparatus may be fabricated with standard CMOS equipment, which provides for low cost; (4) the device consumes very low tuning power (milliwatt range); (5) delivery of thermal energy within the device is locally to just the optical element of interest on the chip with minimal effects on other optical elements over a substrate; and (6) the heat transfer within the device occurs over a microscale distance with a time scale within a microsecond range, enabling very fast tuning.

A more general apparatus in accordance with the embodiments includes a fluidic channel located over a substrate. This particular apparatus also includes at least one of: (1) an optical waveguide optically coupled with an optical resonator each located over the substrate; and (2) a waveguide based Mach-Zender interferometer also located over the substrate, where at least a portion of the optical waveguide or an output portion of the waveguide based Mach-Zender interferometer is located at least in-part within the fluidic channel. This particular apparatus also includes a phase shifter component also located over the substrate but not in the fluidic channel, and operatively coupled with at least one of the optical waveguide, the optical resonator and the waveguide based Mach-Zender interferometer.

A more specific particular apparatus in accordance with the embodiments includes a fluidic channel located over a substrate. This particular apparatus also includes an optical waveguide located over the substrate and partially within the fluidic channel. This particular apparatus also includes an optical resonator located over the substrate, in the fluidic channel and coupled with the optical waveguide. This particular apparatus also includes a phase shifter component located and coupled with the optical waveguide at a location outside of the fluidic channel.

Another more specific particular apparatus in accordance with the embodiments includes a fluidic channel located over a substrate. This particular apparatus also includes a Mach-Zender interferometer located over the substrate and not within the fluidic channel, at least one output of the Mach-Zender interferometer being located within the fluidic channel. This particular apparatus also includes a phase shifter component located outside of the fluidic channel and coupled with one arm of the Mach-Zender interferometer.

Another more specific particular apparatus in accordance with the embodiments includes a fluidic channel located over a substrate. This particular apparatus also includes a Mach-Zender interferometer located over the substrate and not within the fluidic channel, at least one output of the Mach-Zender interferometer being located within the fluidic channel. This particular apparatus also includes an optical resonator coupled with one arm of the Mach-Zender interferometer. This particular apparatus also includes a phase shifter component located outside of the fluidic channel and coupled with the optical resonator.

Another more specific particular apparatus in accordance with the embodiments includes a fluidic channel located over a substrate. This particular apparatus also includes an optical waveguide located over the substrate and partially within the fluidic channel. This particular apparatus also includes an optical resonator located over the substrate, not in the fluidic channel and coupled with the optical waveguide. This particular apparatus also includes a phase shifter component located and coupled with the optical resonator at a location outside of the fluidic channel.

A more general method in accordance with the embodiments includes providing an optofluidic apparatus including: (1) a fluidic channel located over a substrate and including a fluid further including at least one analyte; (2) at least one of: (a) an optical waveguide optically coupled with an optical resonator each located over the substrate; and (b) a waveguide based Mach-Zender interferometer also located over the substrate, where at least a portion of the optical waveguide or an output portion of the waveguide based Mach-Zender interferometer is located at least in-part within the fluidic channel; and (3) a phase shifter component also located over the substrate but not in the fluidic channel, and operatively coupled with at least one of the optical waveguide, the optical resonator and the waveguide based Mach-Zender interferometer. This particular method also includes introducing a light beam into one end of the at least one of the waveguide and the waveguide based Mach-Zender interferometer. This particular method also includes actuating the phase shifter component to detect and manipulate the at least one analyte within the fluid.

BRIEF DESCRIPTION OF THE DRAWINGS

The objects, features and advantages of the embodiments are understood within the context of the Detailed Description of the Embodiments, as set forth below. The Detailed Description of the Embodiments is understood within the context of the accompanying drawings, that form a material part of this disclosure, wherein.

DETAILED DESCRIPTION OF THE EMBODIMENTS

Particular embodiments of electrically tunble integrated optofluidic apparatus are provided. Within the context of the particular embodiments, by using a thermo-optic effect and applying thermal energy through an integrated electric microheater, an optical response of an optofluidic device may be tuned within the context of detecting and manipulating a nanoparticle and/or a biomolecule within a fluid within a fluidic channel that comprises an optofluidic apparatus that yields the optofluidic device. The particular embodiments of the optofluidic apparatus or the optofluidic device use: (1) an optical resonator and at least one waveguide, where the at least one waveguide is located at least in-part within the fluidic channel; or (2) a waveguide based MZI, where at least one output waveguide is located at least in-part within the fluidic channel.

In general, optofluidic apparatus in accordance with the embodiments may be fabricated using silicon-on-insulator (SOI) semiconductor substrates having a buried oxide layer of thickness from about 1 µm to about 3 µm and having a surface silicon semiconductor layer thickness from about 150 to about 300 nanometers. The surface silicon semiconductor layer may be etched or patterned to provide optical resonators, optical waveguides and waveguide based MZI components having a correlating thickness, as well as a width from about 400 nanometers to about 500 nanometers.

In addition, while the embodiments that follow illustrate optofluidic apparatus structures that incorporate an electric microheater for a phase shifter, the embodiments are not necessarily so limited. Rather, embodiments may incorporate alternative phase shifter structures for affecting an index of refraction change for an optical waveguide, an optical resonator or a waveguide based MZI in accordance with the embodiments. Such other structures may include, but are not necessarily limited to a p-i-n diode structure which includes p, i and n silicon region (integrated with a silicon waveguide) from about 1000 nanometers to about 3000 nanometers and p-doped silicon and n-doped silicon concentration in a range from about $10^{19}$ to about $10^{20}$ dopant atoms per cubic centimeter. Particular aspects of such a p-i-n diode based phase shifter component may be found within U.S. Patent Application Pub. No. 2010/0266232, the contents of which are incorporated herein fully by reference. A particular diagram of such a p-i-n diode based phase shifter component is also shown in FIG. 8.

Figure 8:
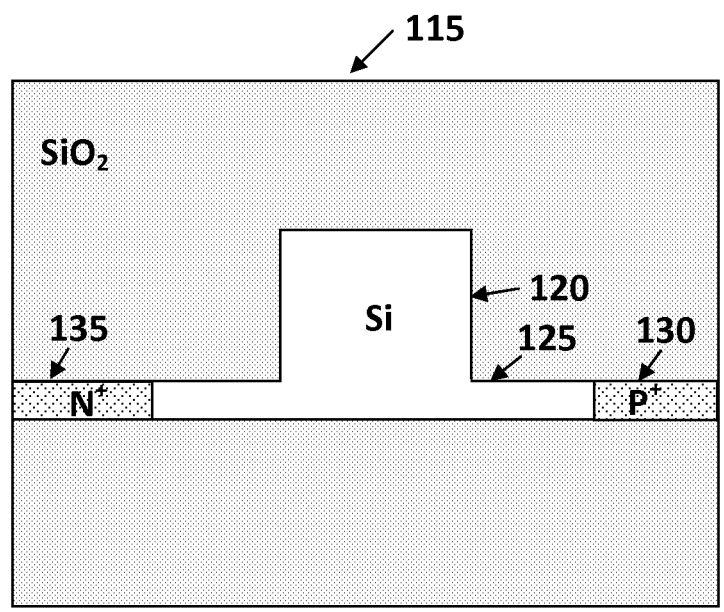
FIG. 8 shows a p-i-n diode based phase shifter in accordance with an alternate embodiment.

FIG. 8 shows a cross-sectional diagram of the p-i-n diode which consists of a strip waveguide 120 formed upon a 50 nm slab layer 125. N+135 and P+130 regions are also illustrated, as well as an upper outline 115 of a silicon oxide passivation layer.

The embodiments also contemplate that portions of an optical waveguide, an optical resonator or a MZI located within a fluidic trench within an optofluidic apparatus in accordance with the embodiments may be biofunctional, such as, for example and without limitation, being antibody biofunctional.

The embodiments also contemplate a variability within structural dimension limitations described below for structural features of a tunable integrated optofluidic apparatus in accordance with the embodiments of at least about +/−20 percent.

I. Particular Embodiments

In one embodiment (i.e., a first embodiment), an optofluidic apparatus for electrical tuning of optofluidic resonators is provided. The optofluidic apparatus comprises an optical resonator optically coupled to two connected waveguides forming an external feedback path for the optical resonator. By placing a phase shifter in the feedback arm, the optical resonator spectrum can be tuned. A portion of this feedback arm is extended outside a fluidic channel region of the optofluidic apparatus where the phase shifter can be realized using a microheater to change the refractive index and correspondingly the spectral response of the resonator.

Figure 1:
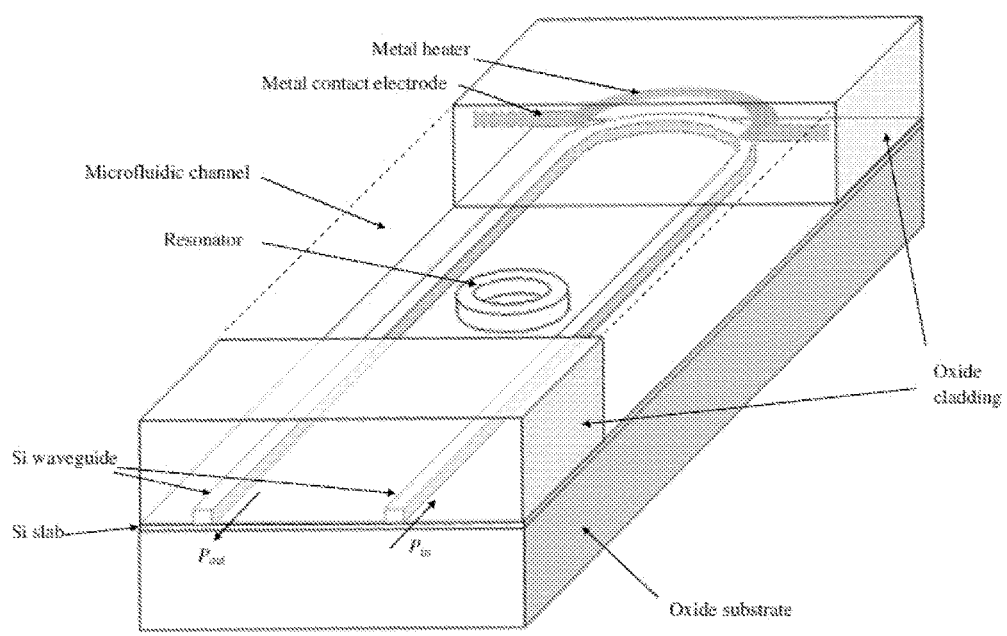
FIG. 1 shows a schematic diagram of an optofluidic apparatus in accordance with a first embodiment including a resonator with an integrated microheater to provide a tunable integrated optofluidic apparatus.

More specifically, FIG. 1 shows a schematic diagram of such an optofluidic apparatus including a resonator with an integrated microheater in accordance with this first embodiment. In this optofluidic apparatus, the resonator architecture may include any traveling-wave resonator (microring, microdisk, racetrack, etc.). As is illustrated in FIG. 1, the resonator has been side-coupled to two connected waveguides forming a feedback loop for the resonator. The resonator is located in a fluidic channel and the waveguide feedback arm is extended outside the fluidic channel. The metal microheater has been implemented on top of the feedback loop with a distance defined by the interface cladding between the waveguide and the metal microheater. The two ends of the heater are connected to the metal electrodes. Except the fluidic channel region, the waveguides are covered by a dielectric cladding which is optically transparent in the operation wavelength of the device. In addition, the cladding has a non-zero thermal conductance to transfer the heat from the metal heater to the waveguide.

Figure 5:
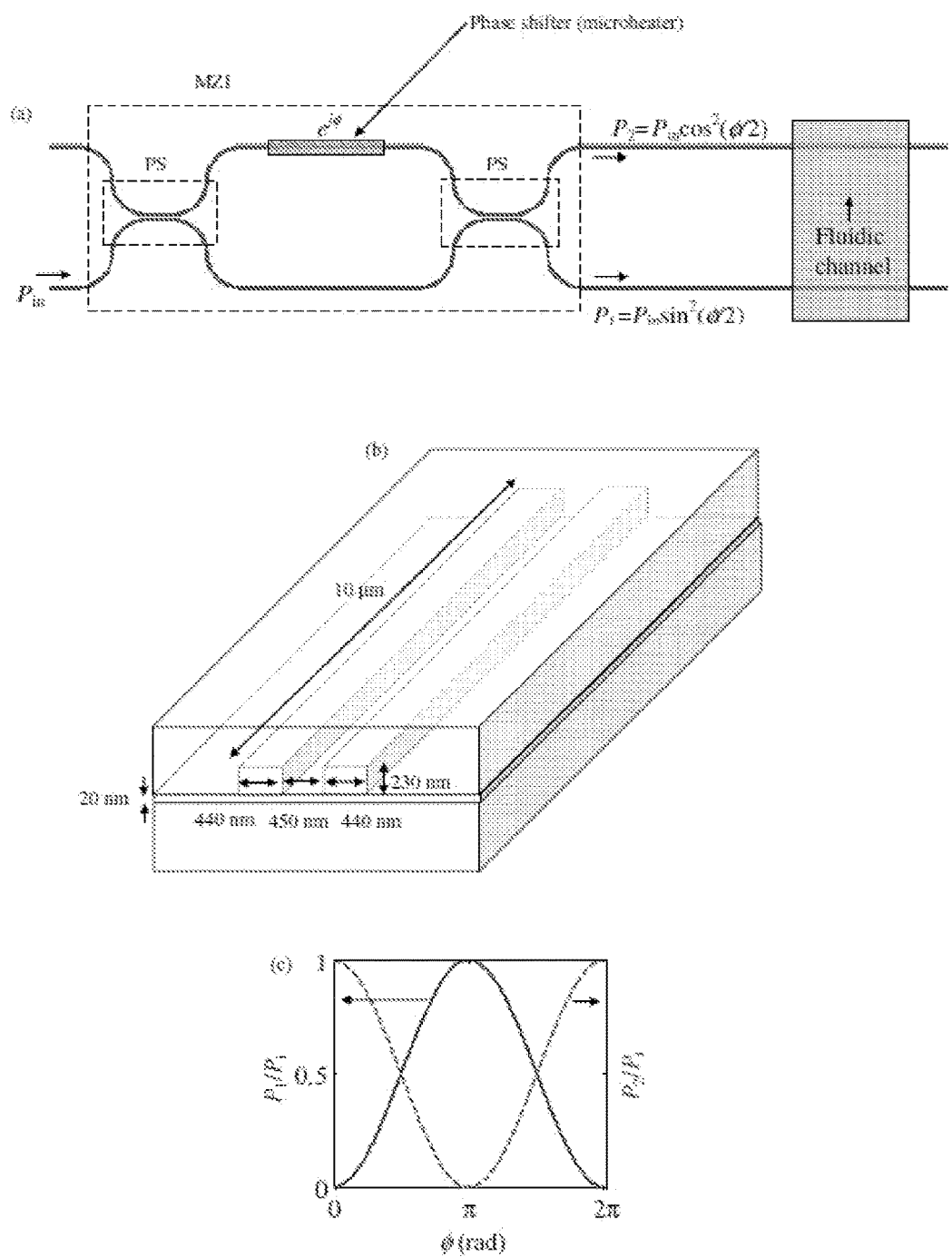
FIG. 5 shows schematic diagrams and anticipated performance characteristics of an integrated MZI with a phase-shifter on one of its arms that provides a tunable integrated optofluidic apparatus in accordance with a second embodiment.

In another embodiment (i.e., a second embodiment), an apparatus for electrically tuning the optical transmission of an optofluidic waveguide is provided (e.g., see FIG. 5). The apparatus comprises a waveguide Mach-Zehnder interferometer (MZI) with a phase-shifter (implemented through a microheater) on one of its arms. The MZI is implemented outside of a fluidic channel of the optofluidic apparatus. One (or both) outport ports of the MZI is (are) extended into the fluidic channel to act as optofluidic waveguide(s). By adjusting the phase of the phase-shifter the optical power in the optofluidic waveguides of this device can vary from zero to maximum (which ideally is equal to the optical power sent into the MZI). The wavelength of a laser is within the operational wavelength range of the MZI. As most MZI devices are broadband devices, the tolerance range of the laser wavelength can be large which makes the device more flexible.

More specifically, FIG. 5(*a*) shows an integrated MZI with a phase-shifter on one of its arms that provides a phase shift φ to the light in that arm. The output ports of the MZI are extended into the fluidic channel of the apparatus as shown by a shaded underlying region. FIG. 5(*b*) shows the structure of the power splitter (PS) used for the design of the MZI. The waveguides are silicon-made, and the dimensions are given such that the PS splits the input power equally into the output arms for the TM polarization. FIG. 5(*c*) shows the dependence of the power in the output ports of the MZI on the phase of the phase shifter.

Figure 6:
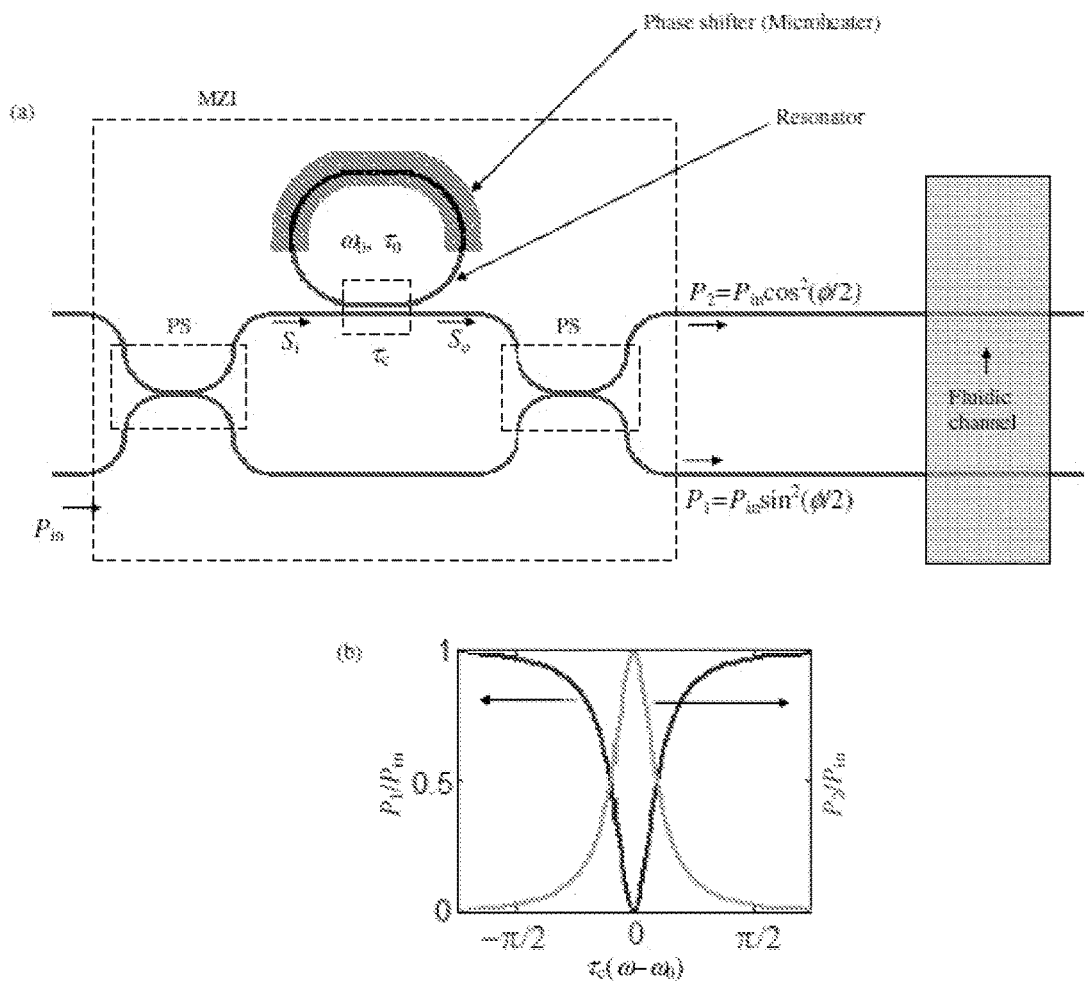
FIG. 6 shows a schematic diagram and anticipated performance characteristics of an integrated MZI with a resonator-based phase-shifter on one of its arms that provides a tunable integrated optofluidic apparatus in accordance with a third embodiment.

In another embodiment (i.e., a third embodiment), the architecture of the phase-shifter (which is implemented as a waveguide-based phase-shifter in the second embodiment) is modified to a resonator-based phase shifter (i.e., see FIG. 6). In this additional apparatus, a microresonator is over-coupled to one arm of the MZI and its resonance is tuned by a microheater implemented on top of the resonator. By changing the resonance, the phase of the outgoing signal in the arm interacting with the resonator changes. An advantage of using the resonator is to make the phase-shifter, and consequently the MZI, device very compact. In addition, the electric power consumption by the microheater becomes much lower compared to that in the apparatus proposed in the second embodiment (and shown in FIG. 5).

More specifically, FIG. 6(*a*) shows an integrated MZI with a resonator-based phase-shifter on one of its arms to provide a phase shift of φ. The output ports of the MZI are extended into a fluidic channel as shown by a shaded underlying region. FIG. 6(*b*) shows the dependence of the power in the output ports of the MZI (which are in the fluidic region) on the phase of the phase shifter.

Figure 7:
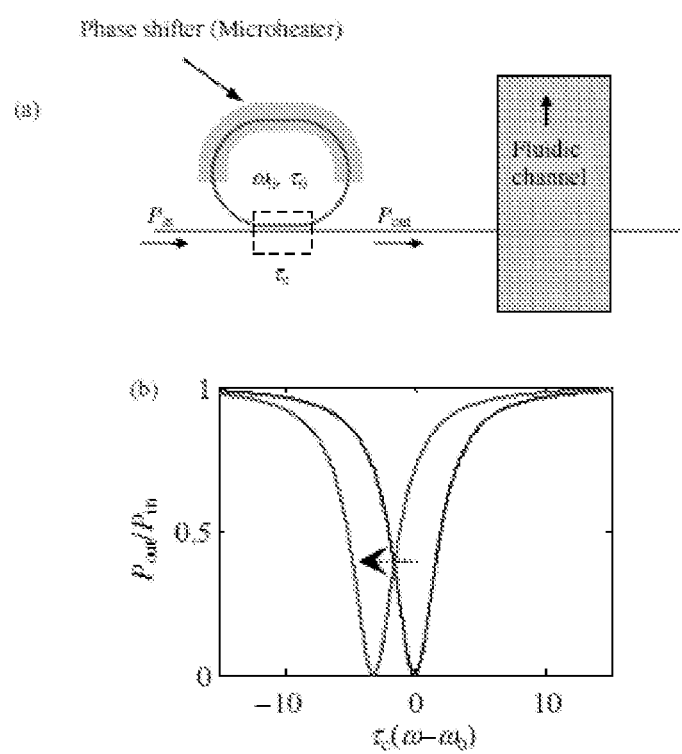
FIG. 7 shows a schematic diagram and anticipated performance characteristics of an optical resonator side-coupled to a waveguide in a critical coupling regime to provide a tunable integrated optofluidic apparatus in accordance with a fourth embodiment.

In another embodiment (i.e., a fourth embodiment), an apparatus for electrically tuning the optical transmission of an optofluidic waveguide is provided (i.e., see FIG. 7). The apparatus comprises a resonator coupled to an optofluidic waveguide outside of a fluidic channel. The waveguide-resonator coupling is in the critical regime which means that at resonance, the transmission through the waveguide is zero. A phase-shifter is implemented on top of the microresonator to tune the resonance wavelength. The phase-shifter is realized using a microheater. Hence, by applying thermal energy one may tune or off-tune a resonance wavelength from a laser source wavelength. As a result of this, the transmission through the waveguide which extends into the fluidic channel may vary from 0 to 100%.

More specifically, FIG. 7(*a*) shows an optical resonator side-coupled to a waveguide in the critical coupling regime. The waveguide is extended into a fluidic channel as shown by a shaded underlying region. A phase-shifter is on top of the resonator to change the resonance wavelength. FIG. 7(*b*) shows the waveguide transmission spectrum before (right) and after (left) a phase-shift is applied. Upon the phase shift, the resonance frequency is shifted accordingly.

Thus the phase-shifter can be used to tune the resonance frequency of the resonator and control the power in the waveguide immersed in a fluid within the fluidic channel.

II. A. Detailed Description of the First Embodiment

In current biophysical and biosensing research, optics has been an indispensible tool and played a major role in exploration of many phenomena all the way down to the single molecule level. Many optical apparatus and optical devices must be aligned or tuned mechanically and/or electrically. To date, most of these apparatus and devices have been bench-top based, making them vulnerable to environmental effects such as vibrations and temperature fluctuations. Miniaturization of these apparatus and devices can alleviate many of these drawbacks with the further advantage of enabling mass production of the apparatus and devices. In addition, microscale apparatus and devices require smaller sample sizes, which is particularly important for expensive or hard-to-obtain samples.

Most demonstrated miniaturized optical apparatus and devices functioning in a microfluidic environment for biological research lack concurrent tunability and control. The aim of the embodiments is to propose novel integrated electrically tunable optofluidic apparatus and devices realizable with conventional microfabrication technology. One may use electric methods for tuning as electronic technology is very mature. Therefore, any physical effect that is at the interface between optics and electronics can be considered for tuning the optical devices. One of these physical effects is the thermo-optic effect in which the refractive index of part of the optical apparatus or device can be modified using thermal energy produced electrically on-chip. The embodiments propose novel architectures to realize simultaneous electronic/photonic/fluidic integration (or namely electro-optofluidic integration) in microscale for controlling and tuning miniaturized optical apparatus and devices in such a platform.

As a demonstration of the integration of microheaters with optofluidic devices on a chip, the embodiments in-part present an electrically tunable optofluidic resonator. Optical micro-resonators hold much promise for sensing and manipulation of nanoparticles and biological molecules. However, because of tolerances in their fabrication, their spectral properties do not always match design specifications. An on-chip tuning mechanism can allow the spectral properties to be brought back to specification. As mentioned above, one may use the thermo-optic effect for tuning a resonator. In order to overcome the traditional challenge in electrical tuning of optofluidic devices due to the need to fabricate an electrical microheater near the device which is immersed in a fluid, one may design structures so that their optical responses (i.e., transmission, resonant characteristics, etc.) are sensitive to a microheater placed outside a fluidic channel. The structure one may utilize here (see FIG. 1) comprises an optical traveling-wave resonator coupled to two connected waveguides forming an external feedback path for the optical resonator. The optical resonator is located inside a fluidic channel. An extension of an optical waveguide out of the fluidic channel has been covered by a dielectric optical material with refractive index smaller than that of the waveguide. By placing a thermo-optic phase shifter n the feedback arm which is isolated from the fluidic channel, the resonator spectrum can be tuned. The phase-shifter is realized using a metal microheater to change the local refractive index of the waveguide. The microheater comprises the metal heating element and the low resistivity metal contact electrodes for applying electric current to the metal heater. Hence, by isolating the microheater from the fluid as shown in this apparatus and device, simultaneous electro-optofluidic integration is possible.

Although the design principles of this apparatus and device are not limited to the choices of the materials used for the waveguides and cladding, one may desirably use optical materials compatible with CMOS technology as they can be manufactured with low cost. Two popular materials with good optical properties for realizing waveguides and resonators are silicon (Si) and silicon nitride ($Si_3N_4$). Silicon is optically transparent in the wavelength range 1300 nm and above, and $Si_3N_4$ is transparent in a much broader wavelength range spanning the entire visible range to infra red (IR) and mid IR. Silicon dioxide ($SiO_2$) can be used as the cladding layer as it has a lower refractive index than that of Si and $Si_3N_4$.

Figure 2:
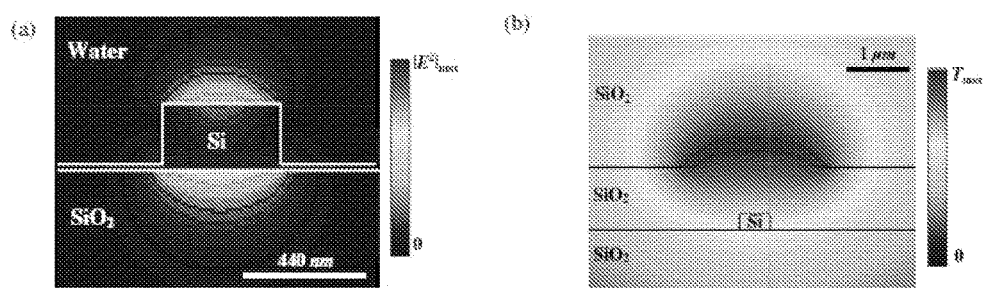
FIG. 2 shows a numerical simulation result for components shown in FIG. 1 for the tunable integrated optofluidic apparatus in accordance with the first embodiment.

In the design and experiments presented here, TM polarization (electric field is predominantly normal to the wafer plane) was used for waveguides and resonators which is suitable for sensing and optical trapping applications, although the apparatus can be designed for the alternative TE (electric field is predominantly parallel to the chip plane) polarization. FIG. 2(a) shows the distribution of the squared magnitude of the electric field for the TM polarization for a silicon waveguide seated on a $SiO_2$ substrate, with water cladding. The waveguide width and height are 440 nm and 250 nm, respectively. There is a 20 nm silicon thin slab at the interface between the waveguide and the underneath oxide layer. This layer is meant for post CMOS wet etching processes wherein hydrofluoric acid (HF) may be used and the presence of the thin Si slab protects the underneath oxide layer from being attacked by the HF.

In summary, FIG. 2(a) shows a distribution of the squared magnitude of the electric field ($|E|^2$) for the TM mode (electric field is predominantly normal to the plane of the chip) of a silicon nanowaveguide with oxide under a thin Si cladding and water over the cladding. FIG. 2(b) shows calculated temperature distribution of a silicon waveguide underneath a metal microheater (made of nickel). The metal heater has been isolated from the silicon waveguide via a 1 µm oxide cladding. The over cladding of the metal heater is also oxide.

The metal used in the metal heater needs to have resistivity and dimensions to provide the required heat energy to the waveguide. Typical metals used are nickel (Ni), chromium (Cr), tungsten (W), and Nichrome (NiCr) because of their high resistivity. For contact electrodes, the typical metals are gold (Au), and aluminum (Al) because of their high conductivity. One may also use aluminum as it is compatible with CMOS fabrication equipment. For the metal heater one may use Ni, Cr, or Nichrome for the same reason. FIG. 2(b) shows a simulation of the temperature distribution around the cross section of a Si waveguide heated with a Ni heater. The Ni width and thickness are 2.5 µm and 200 nm, respectively. The heater has been isolated from the Si waveguide with a 1 µm oxide layer. The over cladding of the Ni heater is also oxide.

Figure 3:
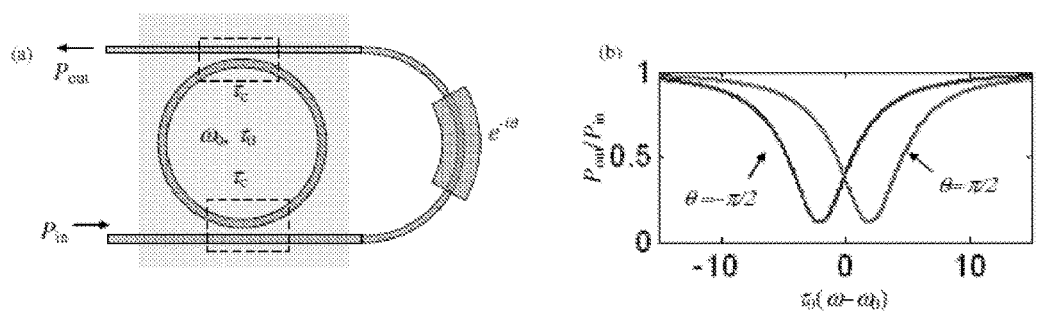
FIG. 3 shows theoretical performance predictions of the tunable integrated optofluidic apparatus in accordance with the first embodiment.

In order to better understand the principle of operation of the devices shown in FIG. 1, one may analyze the same using temporal coupled-mode theory (CMT) and find its transmission response. FIG. 3(a) shows a simplified drawing of the resonator architecture shown in FIG. 1. From CMT analysis one may find the power transmission through this device is $$\frac{P_{out}}{P_{in}} = \left| \frac{i(\omega - \omega_0) + 1/\tau_0 - 2(1 + e^{i(\theta+\theta_0)})/\tau_c}{i(\omega - \omega_0) + 1/\tau_0 + 2(1 + e^{-i(\theta+\theta_0)})/\tau_c} e^{-i(\theta+\theta_0)} \right|^2, \quad (1)$$

where $\omega_0$ and $\tau_0$ are the intrinsic resonance frequency and lifetime of the resonator, respectively, $\tau_c$ is the coupling lifetime between the resonator and each waveguide, $\theta_0$ is the phase shift due to the feedback loop in the absence of heating, and $\theta$ is the additional phase shift induced by the metal heater. From Eq. (1), the net resonance frequency of the device is: $\omega_0' = \omega_0 + 2\sin(\theta+\theta_0)/\tau_c$. Hence, by changing the phase in the feedback arm, the resonance frequency of the resonator can be tuned as shown in FIG. 3(b).

In summary, FIG. 3(a) shows a simplified sketch of a ring resonator side-coupled to two waveguides which are connected at one end. The underlying shaded region is the fluidic channel region. Note that a tunable phase shifter has been added to the connection arm. FIG. 3(b) shows predicted transmission spectrum of the structure in FIG. 3(a) at two different phase shifts. In FIG. 3(b) assumed was $\tau_0 = \tau_c$.

Figure 4:
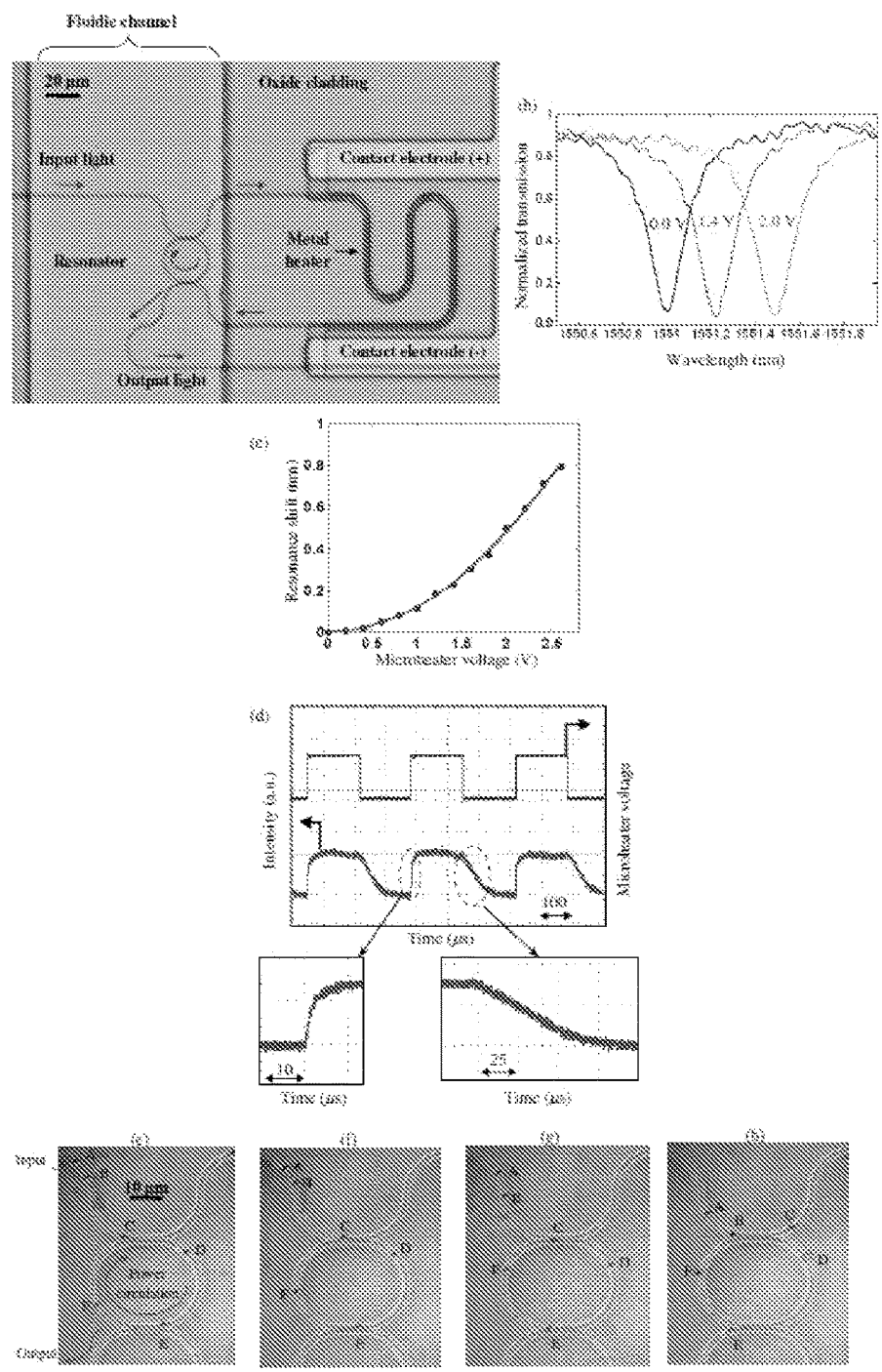
FIG. 4 shows experimental results of the tunable integrated optofluidic apparatus in accordance with the first embodiment.

II. B. Apparatus Fabrication and Experimental Results for the First Embodiment The structure as shown in FIG. 1 has been implemented in a silicon-on-insulator (SOI) platform as silicon has a large thermo-optic coefficient and large refractive index contrast. It is further compatible with many mass manufacturing fabrication processes. The SOI has a silicon thickness of 250 nm and a buried oxide (BOX) thickness of 3 µm. FIG. 4(a) shows a microscope image of the fabricated device. In this device, the waveguides dimensions are 440 nm×250 nm, and the resonator is a racetrack with a bend radius of 10 µm and a straight length of 5 µm. As seen in FIG. 4(a), the resonator is in the fluidic channel and the feedback arm of the device is extended outside the fluidic channel and covered by oxide. The metal heater and contacts are made of nickel (Ni) and aluminum (Al), respectively, and they are on the feedback arm as shown in FIG. 4(a). The fabrication process of the device starts with patterning the waveguides using electron-beam lithography with maN 2403 as a resist mask followed by plasma etching with an etch depth of ~225 nm and leaving an ~25 nm silicon spacer. A 1-µm plasma-enhanced chemical vapor deposition (PECVD) cladding oxide followed by two subsequent steps of lithography and metal evaporation and lift-off defines the metal heater (Ni with 2.5 µm width, 200 nm height, 200 µm length) and the contact electrodes (Al). The metal layers are covered by another 1.5-µm oxide to isolate them from fluid. Finally, with two subsequent steps of optical lithography and wet and dry etching the oxide cladding from the fluidic region (and portion of Al contact which is exposed to off-chip metal probes) is removed. At the end, glass film is bonded to the chip to form the fluidic channel seal which is more suitable for high resolution microscopy.

During an experiment, laser light was coupled into the chip using a tapered lensed optical fiber. Correspondingly, the transmitted light through the chip was collected using another tapered lensed optical fiber and sent to a photodetector. Solution in a microfabricated fluidic channel was exchanged through inlet/outlet holes using syringe pumps. A microprobe was connected to the contact electrodes of the microheater for applying electric voltage. By sweeping the laser wavelength and monitoring the transmitted power through the chip using the photodetector, the spectrum of the resonator was characterized. The spectrum characterization was performed with different voltages applied to the microheater.

One may first demonstrate the tunability of the resonator. FIG. 4(b) shows the spectrum of one of the resonances of the device at different voltages applied to the microheater. The resonance shift due to heating is clearly observed. The FWHM linewidth of this resonance in FIG. 4(b) is ~0.22 nm. The measured resonance shift is in full agreement with prediction. The device consumes extremely low power. For example, for a 2 V voltage, the consumed electric power of the microheater is ~20 mW. FIG. 4(c) shows a comparison of the theoretical and experimental data for resonance shift versus the applied voltage to the microheater. There is a close correspondence between the theory and experiment.

Another interesting study is to know how fast a microheater can respond when applying a voltage to it. This has been shown in FIG. 4(d) wherein by applying a square wave voltage to the microheater the intensity response of the resonator has been measured versus time. From this figure and by measuring the rise time (~6 µs) and fall time (75 µs) of the resonator intensity (in response to the input square wave voltage), one may conclude that the microheater can operate at frequencies above 13 KHz. This shows that the microheater can operate at frequencies >13 kHz, much faster than the characteristic time of nanoparticles in fluids. Hence, a microheater with such response time is very suitable for optofluidic platforms and one may perform a very fast tuning mechanism in the instantly proposed and embodied apparatus using the microheater.

By further optimizing the microheater parameters in the apparatus in accordance with the embodiments, the tuning power and the response time of an integrated microheater can be further improved.

To further verify the tunability of the resonator with the microheater, one may demonstrate dynamic control of optical trapping of nanoparticles by the optofluidic resonator. For this experiment, polystyrene nanoparticles of 790 nm in diameter were injected into the fluidic channel. An input laser wavelength was fixed near the resonance of the resonator. When the resonator was tuned by the microheater to be on resonance, nanoparticles were trapped by both the resonator and waveguide (FIGS. 4(e)-(g)). When the resonator was tuned off resonance, the nanoparticles were no longer trapped by the resonator, but remained to be trapped by the waveguide (FIG. 4(h)).

In the proposed optofluidic resonator, by monitoring any change in the resonator transmission intensity (detected by a photodetector) and accordingly sending a feedback signal to the microheater, one may dynamically tune the resonance wavelength to the laser wavelength to have a stable intensity for the resonator. This can make the embodied device insensitive to a drift or fluctuation in the wavelength of the laser source.

In summary, FIG. 4(a) shows an EM image of a fabricated optofluidic resonator integrated with the microheater in accordance with the first embodiment. FIG. 4(b) shows a resonance spectrum of the resonator at different voltages applied to the microheater as specified in FIG. 4(a). FIG. 4(c) shows resonance wavelength dependence on the applied voltage to the microheater. FIG. 4(d) shows a response time of the resonator. The intensity of the transmitted light was measured (bottom) when a square-wave voltage (top) with an amplitude of 1.5 V was applied to the microheater. This response curve yields a rise time of 6 µs and a fall time of 75 µs as shown in the zoomed figures. Dots are measurements and the solid line is a prediction based on theoretical calculations. FIG. 4(e)-(h) show demonstration of control of nanoparticle trapping using the tunable resonator as shown by captured frames of the video at different snapshot times. The nanoparticles have been labeled in each frame. In the first three frames (e, f, g), the resonance and the laser wavelength are matched. In the fourth frame (h), the heater has off-tuned the resonance and the particles C, D, E, and F have escaped the resonator and furthermore, the particles C and E have been attracted to the waveguides.

III. Considerations Related to Microfluidic Channel Fabrication

Conventional microfluidic fabrication typically uses PDMS as the channel seal to bond to a surface of the fluidic device. Inlet and outlet holes are punched into the PDMS and fluid is injected into and out of the channel through these holes. This can be incorporated in an apparatus in accordance with the embodiments as well. However, PDMS distorts the image when the sample is imaged through it. Therefore one may use glass cover slips instead of PDMS as the fluidic channel seal. Glass cover slips are designed for use in a microscope and provide substantially improved imaging quality. FIG. 4(e) shows a microscope image of the resonator with nanoparticles optically trapped by the resonator. Such imaging quality cannot be obtained with PDMS as a channel seal. For simplicity of fabrication, Parafilm was used to bond the glass to the device's top surface where the fluidic channel was defined. This method may be improved by using wafer bonding techniques available in microfabrication technology. The flow inlet and outlet holes can be perforated into either the glass or the device substrate. For the apparatus used for FIG. 4(e), these holes were in the device substrate (which is silicon) and fluid was introduced from the bottom of the substrate.

IV. A. MZI as a Tuning Element for Optofluidic Waveguides

The foregoing embodiments propose a second application of the integration of microheaters with optofluidic devices on a chip: tuning and power switching in optofluidic waveguides. In comparison with an optical resonator, an optical waveguide has a broad spectral response which makes it suitable for wide-wavelength range applications. That is, the device yields nearly the same performance over a wide wavelength range. This allows the device to function properly in situations in which there are relatively large fluctuations in the wavelength of the laser source. In addition, waveguide-based devices are less sensitive to fabrication-induced dimensional changes in comparison with resonator-based devices.

Since a waveguide is a broadband device, one may propose an apparatus to tune its optical power rather than its spectral properties. The apparatus can be realized using an integrated MZI device residing outside a fluidic channel as shown in FIG. 5(a). The MZI device comprises two 50/50 power splitters (PS) as input and output ports. A phase shifter can be added on one arm of the MZI using a microheater as described earlier. The PS can be a directional coupler which provides a reasonably large bandwidth for the wavelength range of interest. Alternatively, the PS can be a symmetric Y junction. Although Y junctions are very broadband devices, their power losses are higher compared to directional couplers.

FIG. 5(b) shows an example of the structure of the PS designed for silicon waveguides in SOI platform. The waveguide dimensions are 440 nm (width) and 250 nm (height including a 20-nm thin Si slab), and the gap between the waveguides is 450 nm. The coupler arms split with bend waveguides (not shown in FIG. 5(b)) with a bend radius of 12 µm. The upper cladding of the waveguides is an oxide material. Incorporating the effect of the bend region into the coupling between the two parallel waveguides, one may find (from theoretical analysis) a straight length of 10 µm for the coupling region in order to have 3-dB power splitting. The output ports of the MZI in FIG. 5(a) have been extended into the fluidic channel for optical sensing and manipulation purposes. FIG. 5(c) shows the variation of the power at output ports of the MZI with respect to the phase change induced by the phase-shifter. From this FIG. 5(c), one may clearly see that by adjusting the phase of the phase-shifter, the optical power can be totally switched from one waveguide to the other waveguide at the output of the MZI. Therefore, by controlling the phase-shifter using a microheater, one may switch the optical power in one waveguide from zero to 100%.

The fabrication process for the apparatus depicted in FIG. 5(a) is similar to that explained for the fabrication of the apparatus in FIG. 1. The microheater is made of Ni metal with Al as contact electrodes. For efficient heat transfer between the heater and the waveguide, the Ni heater is placed 1 µm above the waveguide with an oxide as the interface material. This oxide thickness is enough to optically isolate the waveguide from the metal heater and, therefore, alleviate metal-induced optical loss. From a theoretical analysis, for a nickel heater with a thickness of 200 nm, width of 2.5 µm and length of 300 µm along the waveguide, a phase-shift of π is obtained by applying 2 V voltage to the heater.

The proposed optofluidic waveguide switch shown in FIG. 5(a) is compact and power efficient while working over a large wavelength range. This can make the device insensitive to fluctuation in the wavelength of the laser source.

IV. B. Resonator Enhanced MZI as a Tuning Element for Optofluidic Waveguides As a third application, the embodiments propose a device similar in architecture to that proposed in FIG. 5(a), but with a difference in the phase-shifter architecture which is realized using a microresonator in one arm of the MZI as shown FIG. 6(a). A resonator phase-shifter increases device compactness and reduces power consumption. In this scenario, the resonator is strongly coupled to the waveguide so that the transmission of the waveguide is like an all-pass filter with a unity power transmission and only a phase change. To better understand the principle of operation of the device, the response of the resonator coupled to the waveguide can be obtained using temporal coupled-mode theory as $$\frac{S_o}{S_i} = \frac{i(\omega - \omega_0) + 1/\tau_0 - 1/\tau_c}{i(\omega - \omega_0) + 1/\tau_0 - 1/\tau_c}, \quad (2)$$

where $S_i$ and $S_o$ are the complex amplitude of the waveguide mode before and after interaction with the resonator in the upper arm of the MZI and they are normalized such that their squared magnitudes represent the waveguide mode power. When the resonator is strongly coupled to the waveguide ($\tau_c \ll \tau_0$), Equation (2) can be approximated as $$\frac{S_o}{S_i} = \frac{i(\omega - \omega_0) - 1/\tau_c}{i(\omega - \omega_0) + 1/\tau_c}. \quad (3)$$

Eq. (3) has a constant magnitude of 1 and a phase response of $\phi = -2 \tan^{-1}[\tau_c (\omega - \omega_0)]$. Hence by adjusting ($\omega - \omega_0$), one may tune the phase response in the upper arm of the MZI. Since w is the laser source frequency and fixed, by tuning $\omega_0$ using a microheater one may realize the required phase shift.

The fabrication process for the apparatus depicted in FIG. 6(a) is similar to that explained for the fabrication of the apparatus in FIG. 1. In an actual fabricated device, the operational wavelength bandwidth is determined by the coupling lifetime ($\tau_c$) of the resonator. Resonators with larger $\tau_c$ provide the phase shift in a narrower bandwidth. This requires a laser with a linewidth narrower than the linewidth of the spectrum of the resonator phase-shifter. On the other hand, a narrow linewidth phase-shifter requires less thermal energy in order to be spectrally shifted.

IV. C. Resonator as a Tuning Element for Optofluidic Waveguides

This device is realized using a microresonator residing outside a fluidic channel as shown in FIG. 7(a). The resonator is coupled to a waveguide which is extended inside the fluidic channel. A phase-shifter has been implemented on top of the resonator. By adjusting the phase of the phase shifter, the resonance frequency of the resonator is tunable. The resonator works in the critical coupling regime (i.e., the intrinsic lifetime of the resonator ($\tau_0$) is equal to the coupling lifetime of the resonator ($\tau_c$) to the waveguide). In this coupling scheme, power transmission through the waveguide goes to zero at the resonance as shown in FIG. 7(b). As shown in FIG. 7(b), by adjusting the phase of the phase-shifter transmission through the waveguide can change from 0 to 100%. As a result, the optical power sent to the fluidic region can be switched on and off.

The fabrication process for the apparatus depicted in FIG. 7(a) is similar to that explained for the fabrication of the apparatus in FIG. 1. In the actual fabricated device, the operational wavelength bandwidth is determined by the intrinsic lifetime (or equivalently the quality factor) of the resonator. Resonators with larger quality factors make the bandwidth narrower. This requires a laser with a linewidth narrower than the linewidth of the device. On the other hand, a narrow linewidth resonator requires less thermal energy in order to be spectrally shifted.

V. Applications

Laser light of an appropriate wavelength can be a nondestructive tool in biophysical studies, drug delivery, and pharmaceutical applications. All the embodied apparatus and devices proposed in this invention are laser-based and can have many applications in biological sciences including fundamental physical investigations of cells and single molecules, drug delivery to a point of interest, and general pharmaceutical applications. The proposed embodied apparatus and devices in this invention aim to enhance control and information throughput while miniaturizing device dimensions.

Specific applications of the embodied apparatus and devices include (but are not limited to): (1) manipulation and detection of single biological molecules; (2) detection and sensing of micro and nanoparticles; (3) optical trapping of micro/nano particles; (4) particle monitoring and counting; (5) cell sorting and trapping; (6) bacteria sorting and trapping; (7) biochemical analysis (monitoring biochemical reaction using the apparatus); (8) biosensing; (9) personalized medicine; (10) water quality evaluation; (11) pathogen detection; (12) transport and separation of biomolecules; (14) detection of viruses; (15) absorption spectroscopy of biomolecules; (16) enhancing the florescence for biomolecule and cell imaging; and (17) enhancing the Raman sensing of biomolecules.

All references, including publications, patent applications, and patents cited herein are hereby incorporated by reference in their entireties to the same extent as if each reference was individually and specifically indicated to be incorporated by reference and was set forth in its entirety herein.

The use of the terms "a" and "an" and "the" and similar referents in the context of describing the embodiments (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it was individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

We claim:

1. An optofluidic apparatus comprising:
   only a single fluidic channel located over a substrate;
   a Mach-Zehnder interferometer located over the substrate and not within the single fluidic channel, at least one output of the Mach-Zehnder interferometer being located within the single fluidic channel; and
   a phase shifter component located outside of the single fluidic channel and coupled with one arm of the Mach-Zehnder interferometer.

2. The optofluidic apparatus of claim 1 further comprising:
   a light source coupled with an input of the Mach-Zehnder interferometer; and
   a photodetector coupled with an output of the Mach-Zehnder interferometer.

3. The optofluidic apparatus of claim 2 wherein the light source is in the visible range.

4. The optofluidic apparatus of claim 2 wherein the light source is in the ultraviolet range.

5. The optofluidic apparatus of claim 1 wherein the phase shifter component comprises an electric microheater.

6. The optofluidic apparatus of claim 1 wherein the phase shifter component comprises a p-i-n diode.

7. A method for operating an optofluidic apparatus comprising:
   providing an optofluidic apparatus including:

only a single fluidic channel located over a substrate and including a fluid further including at least one analyte; and a waveguide based Mach-Zehnder interferometer also located over the substrate;

where at least an output portion of the waveguide based Mach-Zehnder interferometer is located at least in-part within the fluidic channel; and a phase shifter component also located over the substrate but not in the fluidic channel, and operatively coupled with the waveguide based Mach-Zehnder interferometer;

introducing a light beam into one end of the waveguide based Mach-Zehnder interferometer; and actuating the phase shifter component to detect and manipulate the at least one analyte within the fluid.

8. The method of claim 7 wherein the at least one analyte comprises at least one of a nanoparticle and a biomolecule.

9. The method of claim 7 wherein the at least one analyte is detected and manipulated without changing a temperature of the fluid.

\* \* \* \* \*